United States Patent [19]

Poisson et al.

[11] 4,307,221
[45] Dec. 22, 1981

[54] FIRE-RESISTANT (CO)POLYCARBONATES CONTAINING ALKALINE DIESTERS OR HEMIESTERS OF PHOSPHONIC ACIDS

[75] Inventors: Pierre Poisson, Bernay; Georges Sturtz, Brest, both of France

[73] Assignee: Ato Chimie, Paris, France

[21] Appl. No.: 117,506

[22] Filed: Feb. 1, 1980

[30] Foreign Application Priority Data

Feb. 5, 1979 [FR] France ................ 79 02836

[51] Int. Cl.$^3$ .......................................... C08G 63/62
[52] U.S. Cl. ............................................. 528/167
[58] Field of Search ............................... 528/167

[56] References Cited

U.S. PATENT DOCUMENTS

| | | | |
|---|---|---|---|
| 3,378,523 | 4/1968 | Caldwell et al. | 528/167 |
| 3,525,711 | 8/1970 | Jenkner | 260/47 |
| 3,847,866 | 11/1974 | Bredereck et al. | 528/167 |

FOREIGN PATENT DOCUMENTS

| | | |
|---|---|---|
| 1199499 | 8/1965 | Fed. Rep. of Germany . |
| 1495378 | 2/1969 | Fed. Rep. of Germany . |
| 2114236 | 10/1972 | Fed. Rep. of Germany . |
| 1402407 | 6/1965 | France . |

Primary Examiner—Maurice J. Welsh

Attorney, Agent, or Firm—Bacon & Thomas

[57] ABSTRACT

New fire-resistant transparent (co)polycarbonates containing alkaline diesters or hemiesters of bis (hydroxy-4-phenyl) alkylphosphonic acids, with the following general formulae (I) or (II):

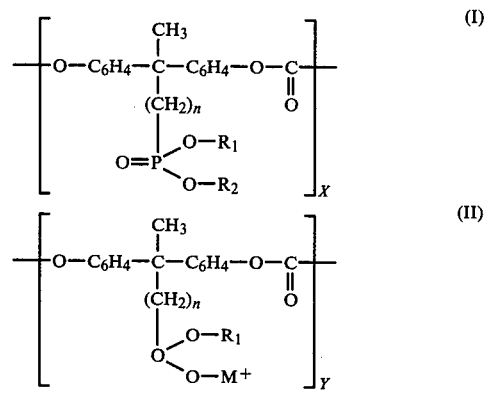

(I) where $n = 1, 2$ or $3$
(II) where $n = 0, 1, 2$ or $3$ and
where $R_1$ or $R_2$ is a methyl or ethyl radical, and M is an alkaline metal, such as sodium or potassium.

19 Claims, No Drawings

FIRE-RESISTANT (CO)POLYCARBONATES CONTAINING ALKALINE DIESTERS OR HEMIESTERS OF PHOSPHONIC ACIDS

This invention concerns new (co)polycarbonates containing alkaline diesters or hemiesters of bis (hydroxy-4-phenyl) alkylphosphonic acids; and possessing fire-resistant properties.

Polycarbonates are themselves self-extinguishing materials. For a number of uses in the building, domestic appliance and aeronautical engineering fields, however, this intrinsic fire resistance needs to be improved.

Products already used to fire-proof polycarbonates include halides such as decabromodiphenyl ether as additive, or tetrachloro- or tetrabromobisphenol A as polycondensation agent. But when these products are used, there is a danger of toxic, corrosive halohydric acids (HCl or HBr) being released during combustion.

Many polymers can be fireproofed with phosphorus derivatives, which do not give off any toxic or corrosive fumes during combustion. Consideration has been given to using them to fireproof polycarbonates. Such derivatives have a combustion-inhibiting effect, believed to arise from the formation of sooty residues and non-combustible matter, which prevent combustible gases from spreading so quickly to the combustion zone.

Previous patent applications concerning inclusion of the phosphorus atom in the macromolecular chain comprise Fr No. 1.402.407, DT No. 1.199.499, U.S. Pat. No. 3,378,523 and JA No. 75.72.936, containing descriptions of copolycondensates with the formula:

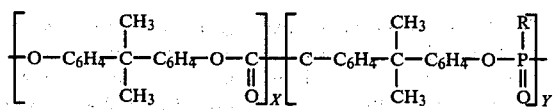

The phosphonic function shows poor resistance to hydrolysis, which causes chemical deterioration of the macromolecular chain. More stable polymers with the formula:

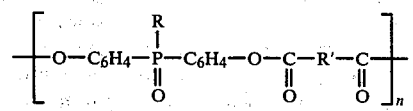

have been produced by synthesis (cf. *Journal of Polymer Science* 1974, p. 2537) from phosphine oxides. But phosphine oxides present practical difficulties for synthesis. Iliopoulos and Wieder (*Angewandte Chem.* 1965, 77, 618) obtained a polycarbonate containing "hanging" phosphonate groups, by interfacial reaction between dimethyl bis(hydroxy-4-phenyl)1.1 ethylphosphonate and phosgene:

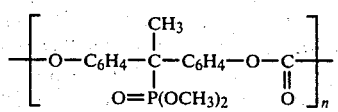

The phosphonate groups are outside the molecular chain, which means that these polymers are not very subject to hydrolysis-type deterioration.

However, they are too rigid for certain uses, and have high glass transition points, making them difficult to work. Furthermore, the use of large amounts of a phosphorus derivative in the polymer can make the resulting copolymer too expensive.

This invention offers a way of overcoming such drawbacks.

It concerns (co)polycarbonates containing alkaline hemiesters or diesters of bis(hydroxy-4-phenyl) alkyl phosphonic acids with the following general formulae:

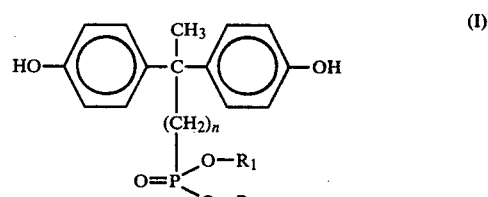

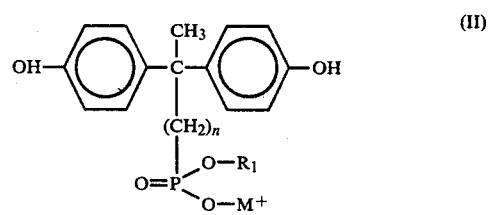

(I) where $n = 1, 2$ or $3$;

(II) where $n = 0, 1, 2$ or $3$; and where $R_1$, $R_2$ is a methyl or ethyl radical; and M is an alkaline metal, sodium or potassium.

French patent application No. 78 35.753 contains a description of products with formula (I) above, and their preparation.

Hemiesters according to formula (II) are obtained from diesters according to formula (I).

These products, according to formula (I) or (II), are used to produce either homopolycarbonates with the formula:

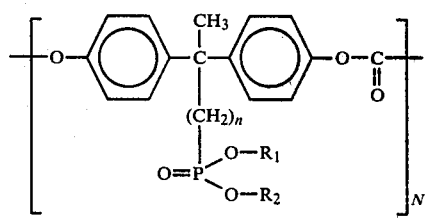

which can be used as fireproofing additives for other polymers, or copolycarbonates by cocondensation with other bisphenols, such as bisphenol A, which produces products with the formula:

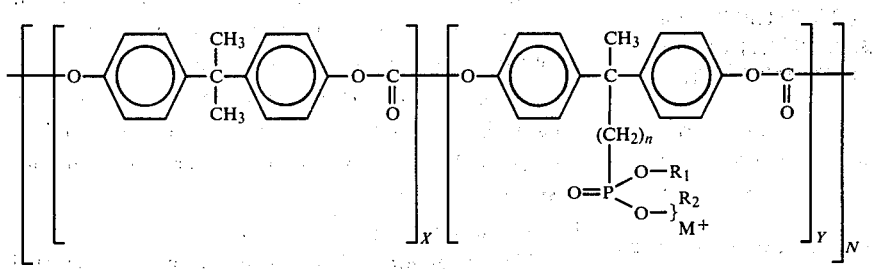

where
X and Y represent the molar proportions occuring in the recurrent group,
and N indicates repetition.

For the same Limit Oxygen Index, between 31 and 36, the molar proportion of diesters has to be from 10 to 75% of total monomers present, while with alkaline hemiesters the proportion is only 0.5 to 2%.

An "Internal plasticization" effect, which reduces the glass transition point Tg, can be obtained by choosing R in the group

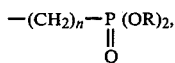

and the length of the aliphatic chain - $(CH_2)_n$ when $n=1$, 2 or 3. This effect is permanent; it allows the product to be used at lower temperatures, and ensures less rigid materials.

The presence of

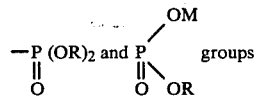

can also confer internal adhesiveness and tinctorial affinity to plastic materials.

These new polycarbonates and copolycarbonates are transparent, and also possess high heat resistance at 250° C., so that they can be used without any risk of molecular deterioration.

Suitable dialkyl bis(hydroxy-4-phenyl)alkylphosphonates comprise dimethyl bis(hydroxy-4-phenyl) 2.2 propylphosphonate, diethyl bis(hydroxy-4-phenyl) 2.2 propylphosphonate, and dimethyl bis(hydroxy-4-phenyl) 3.3 butylphosphonate.

These bisphenol phosphonates can be used on their own, or mixed with other bisphenols such as bisphenol A.

Suitable alkaline phosphonic hemiesters comprise methyl and sodium bis(hydroxy-4-phenyl)1.1 ethylphosphonate, methyl and potassium bis(hydroxy-4-phenyl)1.1 ethylphosphonate, methyl and sodium bis(hydroxy-4-phenyl) 2.2 propylphosphonate, methyl and potassium bis (hydroxy-4-phenyl) 2.2 propylphosphonate, methyl and sodium bis(hydroxy-4-phenyl) 3.3 butylphosphonate, and ethyl and potassium bis (hydroxy-4-phenyl) 2.2 propylphosphonate.

These new polycarbonates and copolycarbonates are produced by the interfacial phosgenization process, already known in the existing art. The method consists of dissolving the bisphenols in an aqueous solution of an alkaline hydroxide, preferably caustic soda or potash, with a 10 to 50% molar excess in relation to bisphenol, and adding a suitable non-mixing solvent to dissolve the resulting polycarbonate. Such solvents comprise chlorinated hydrocarbons such as methylene chloride, chloroform and 1.2 dichlorethane.

Sodium or potassium bisphenolates are made to react with phosgene, which may be added in a 20% solution in toluene, or in gaseous form.

The reaction takes place at between 5° and 25° C., and preferably between 5° and 15° C. Tertiary amines, such as triethylamine, or quaternary ammonium salts or phosphonium salts, may be used as catalysts.

Ammonium triethylbenzyl chloride and phosphonium triphenylbenzyl chloride result in larger masses. The molar proportion of catalyst to bisphenols is between 1 and 5% and preferably between 1 and 3%. The phosgenization reaction may also be performed in the presence of a chain-limiting agent, such as an alcohol like methanol or ethanol, or a phenol like phenol or dimethyl 2.6 phenol. The molar proportion of phenol to bisphenols is between 1 and 2%.

When phosgene has been added, polycondensation continues for a period of ½ hour to 3 hours, and preferably 1 to 2 hours, at a temperature of approximately 30° C.

Methods known in the existing art are used to separate the polycarbonates. For example, the aqueous phase may be separated out, and the organic phase washed several times in water, until the washing water becomes neutral. The organic phase is then poured into a non-solvent of the polycarbonate, such as ether. The polycarbonate precipitate is drained and dried at reduced pressure, at a temperature of 100° to 120° C., for 24 to 48 hours.

There are many recognized ways of testing the combustion properties of polymers; but measurement of the oxygen index is increasingly accepted as a way of determining the fire-resistant properties of materials. It consists of assessing polymer combustion in an atmosphere containing a given, variable concentration of oxygen. The limit oxygen index (LOI) is obtained by the formula:

$$\frac{(O_2)}{(O_2) + (N_2)} \times 100$$

where $(O_2)$ is the oxygen concentration and $(N_2)$ the nitrogen concentration of the combustion mixture in which the sample of material is burnt. ASTM standard D-2863,70 provides fuller details.

Molecular weights were measured by means of gel-permeable chromatography (GPC). This method consists of injecting the solution into a Waters GPC 200 appliance, operating under the following conditions:
set of six columns of styragel with a porosity from 106 to 700 Å;

solvent: THF at atmospheric temperature, flow-rate 1.25 ml/min.;

quantity injected: 2 ml at 0.25% (weight/volume). Results were obtained by universal calibration, using Waters polystyrene narrow fractions.

Glass transition points Tg were measured on a Heraeus TA 500 S apparatus, operating under the following conditions:

cell: differential scanning calorimetry (DSC);
reference: empty capsule;
heating velocity = 10° C. min$^{-1}$.

The product was heated once and cooled down quickly, and the glass transition point was measured during the second heating.

The heat stability of the polycarbonates was measured on a Mettler HE 20 thermobalance, equipped with a linear temperature programmer, and operating under the following conditions:

weight of sample 100 mg;
atmosphere: air;
temperature pattern: 6° C. min$^{-1}$, then 250° C. isotherm.

The invention is illustrated by, without being confined to, the following examples.

EXAMPLE 1

Diethyl bis (hydroxy-4-phenyl) 2.2 propylphosphonate polycarbonate

Using apparatus consisting of a 1-liter balloon-flask with 5 tubes, equipped with an agitator, upward cooler, thermometer, inlet bulb, and an electrode to measure the pH-value, 36.4 g diethyl bis (hydroxy-4-phenyl) 2.2 propylphosphonate (0.1 mole) were dissolved in 150 ml of a 1.56 N soda solution obtained by dissolving 9.4 g soda pellets (0.235 mole) in 150 ml ion-exchanged water.

0.35 g ammonium triethylbenzyl chloride (molar ratio to bisphenol phosphonate 1.5), 0.1 g phenol (molar ratio to bisphenol phosphonate 1), and 170 ml methylene chloride, which had first been passed through a 4 Å molecular sieve to remove stabilization alcohols (methanol and ethanol), were then added in turn to the solution.

The reaction mixture was cooled in a flow of nitrogen to approximately 5° C., then 58 ml (0.11 mole) of a toluene solution containing 20% phosgene were added, while the mixture was agitated strongly.

The temperature was kept between 5° and 15° C. The pH-value was above 9 through the period of addition of the phosgene solution.

When this was completed, the emulsion was kept strongly agitated in a flow of nitrogen for 1 hour at 30° C. (to within 2° C.). It was then cooled, diluted with 300 ml CH$_2$Cl$_2$, and decanted.

The organic phase was washed several times in 150 ml water, until the water used for washing became neutral, and it was then poured slowly into 1.7 liter of ether, with the agitator in operation.

The polycarbonate precipitate was partly dried, crushed, then dried at 100° to 110° C., at reduced pressure, for at least 24 hours. There was a 76.5% yield of polycarbonate, using this method.

Apparent molecular weights are given in relation to bisphenol A homopolycarbonate:

$\overline{M_w}$ = 20 700   ($\overline{M_w}$ = Weight Average Molecular Weight)

$\overline{M_n}$ = 7 600   ($\overline{M_n}$ = Number Average Molecular Weight)

Polydispersiveness index I = 2.7   $\left( I = \dfrac{\overline{M_w}}{\overline{M_n}} \right)$

| Elementary analysis: | Calculated % | Experimental % |
|---|---|---|
| Phosphorus | 7.9 | 8.27 |

LOI = 29
Glass transition point Tg = 118° C.
NMR $^1$H spectrum (solvent CDCl$_3$):

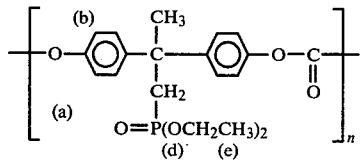

δ = 7.22 ppm (singlet)   8 Ha
δ = 3.75 ppm (quintuplet)   4 Hd
δ = 2.68 ppm (doublet)   2 Hc; JP-Hc = Hz
δ = 1.95 ppm (singlet)   3 Hb
δ = 1.12 ppm (triplet)   6 He

EXAMPLE 2

Bis (hydroxy-4-phenyl) 2.2 propane polycarbonate

This test was done for purposes of comparison with bisphenol A.

The operating procedure was the same as in Example 1. 22.8 g (0,1 mole) of bisphenol A were used.

There was a 90% yield of bisphenol A polycarbonate.

Molecular weights (by GPC):

$\overline{M_w}$ = 69 600
$\overline{M_n}$ = 20 500
I = 3.4

| Elementary analysis: | Calculated % | Experimental % |
|---|---|---|
| Carbon | 75 | 75.06 |
| Hydrogen | 5.46 | 5.63 |

Glass transition point Tg = 155° C.
1H spectrum (solvent CDCl$_3$)

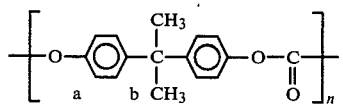

δ = 7.187 ppm (s) 8 Ha
δ = 1.67  ppm (s) 6 Hb
LOI = 27.5

EXAMPLES 3, 4 and 5

Bisphenol A (B.A.) and dimethyl bis (hydroxy-4-phenyl) 2.2 propylphosphonate copolycarbonates Compositions contain a molar proportion of 90 to 50% bisphenol A. The same operating procedure was used as in Example 1. Tests were performed on 0.1 mole of dihydroxylated compounds. Results are shown in Table I: Bisphenol A and dimethyl bis (hydroxy-4-phenyl) 2.2 propylphosphonate copolycarbonates with the formula:

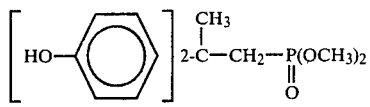

TABLE I

| Example No. | Molar % Biphenol A Biphenol phosphonate | GPC Mw | Mn | I | Elementary analysis Phosphorus calc. % | Exper. % | Yield % | Tg °C. | LOI | Heat resistance ΔP % 2 hrs at 250° C. |
|---|---|---|---|---|---|---|---|---|---|---|
| 3 | 90 | | | | | | | | | |
|   | 10 | 38680 | 13160 | 2.8 | 1.16 | 1.01 | 86 | 152 | 31 | 0.2 |
| 4 | 75 | | | | | | | | | |
|   | 25 | 25050 | 9870 | 2.5 | 2.73 | 2.33 | 77 | 151 | 33 | 0.4 |
| 5 | 50 | | | | | | | | | |
|   | 50 | 15400 | 6120 | 2.5 | 4.99 | 4.20 | 71 | 141 | 34 | |

EXAMPLE 6

Dimethyl bis (hydroxy-4-phenyl) 2.2 propylphosphonate polycarbonate

Using the same apparatus as in Example 1, 16.66 g dimethyl bis (hydroxy-4-phenyl) 2.2 propylphosphonate (0.0496 mole) were dissolved in 200 ml of an 0.75 N soda solution.

1 g of 98% triphenylbenzylphosphonium chloride (2.56×10⁻³ moles) and 100 ml methylene chloride were then added in turn to the solution.

The reaction mixture was cooled in a flow of nitrogen to approximately 5° C., then 29 ml of a toluene solution containing 20% phosgene (0.055 mole) were added while the mixture was agitated strongly.

The temperature was kept between 5° and 10° C. The pH-value was above 13 throughout the period of addition of the phosgene solution.

When this was completed, the emulsion was strongly agitated for 1 hour at 30° C. (to within 2° C.). It was then cooled, diluted with 125 ml CH₂Cl₂, and decanted.

The organic phase was washed several times in water until the water used for washing became neutral, and it was then poured slowly into 1 liter of ether, with the agitation in operation.

The polycarbonate precipitate underwent the process described in Example 1.

There was an 80.2% polycarbonate yield.

Mw = 31 100
Mn = 9 200
I = 3.5

| Elementary analysis: | Calculated % | Experimental % |
|---|---|---|
| Phosphorus | 8.5 | 7.72 |

Tg = 142° C.
LOI = 36.5
NMR ¹H spectrum (solvent CDCl₃):

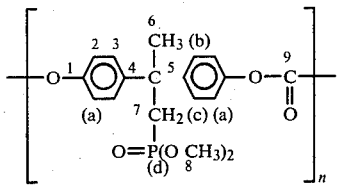

δ = 7.25 ppm (singlet)        8 Ha
δ = 3.37 ppm (doublet)        6 Hd, JP-Hd = 11 Hz
δ = 2.67 ppm (doublet)        2 Hc, JP-Hc = 20 Hz
δ = 1.937 ppm (singlet)       3 Hb NMR ¹³C spectrum (solvent CDCl₃):
δ = 152.1 ppm         C₁
δ = 149.31 ppm        C₉
δ = 146.9–146,19 ppm  C₄
δ = 128.38 ppm        C₃
δ = 120.52 ppm        C₂
δ = 52.17–51,71 ppm   C₈
δ = 43.79 ppm         C₅
δ = 33.26 ppm         C₇
δ = 29.04 ppm         C₆

EXAMPLES 7 and 8

Bisphenol A and dimethyl bis (hydroxy-4-phenyl) 2.2 propylphosphonate copolycarbonates produced by the same procedure as in Example 6

Compositions contained a molar proportion of 25 to 50% bisphenol A. Results are shown in Table 2: Bisphenol A and dimethyl bis (hydroxy-4-phenyl) 2.2 propylphosphonate copolycarbonates produced by the same procedure as in Example 6.

TABLE II

| Example No. | Molar % Bisphenol A Bisphenol phosphonate | GPC Mw | Mn | I | Elementary analysis Phosphorus calc. % | Exper. % | Yield % | Tg °C. | LOI |
|---|---|---|---|---|---|---|---|---|---|
| 7 | 50 | | | | | | | | |
|   | 50 | 157600 | 15000 | 10.5 | 4.99 | 4.80 | 65 | 151.5 | 35 |
| 8 | 25 | | | | | | | | |
|   | 75 | | | | 6.88 | 5.80 | 69 | 158 | 36 |

EXAMPLE 9

Dimethyl bis (hydroxy-4-phenyl) 3.3 butylphosphonate polycarbonates

The operating procedure was the same as in Example 6.

There was a 68% yield of polycarbonate.

Elementary analysis: Calculated % Experimental %
Phosphorus 8.5 7.72
Tg = 101° C.
LOI = 0.35
—NMR $^1$H spectrum (solvent CDCl$_3$):

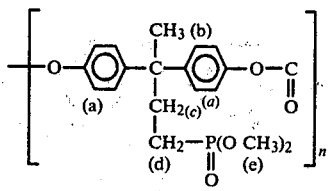

δ = 7.25 ppm (singlet)    8 Ha
δ = 3.71 ppm (doublet)    6 He, JP-He = 11 Hz
δ = 1.62 ppm (singlet)    3 Hb Hc and Hd protons come out in the form of a block extending from 2.62 to 2 ppm, and under Hb protons.

EXAMPLES 10 to 12

Copolycarbonates of bisphenol A and methyl and sodium bisphenol phosphonate with the following structure:

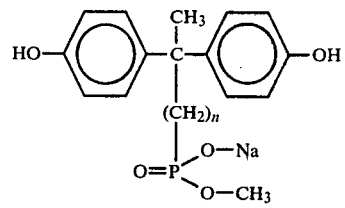

where
n=0 (compound A)
n=1 (compound C)
n=2 (compound E)

Compositions contained 1% moles compounds, A, C and E to 99% moles bisphenol A.

Tests were performed on 0.1 mole dihydroxylated compounds. The operating procedure was the same as in Example 1. Results are shown in Table III: Copolycarbonates of bis(hydroxy-4-phenyl) 2.2 propane (99% moles) and methyl and sodium bisphenol phosphonates with the following structure:

TABLE III

| Example No. | Molar % Biphenol A Biphenol phosphonate | GPC Mw | GPC Mn | I | Elementary analysis Phosphorus Calc. % | Exp. % | Sodium Calc. % | Exp. % | Yield % | LOI | Heat resistance 2 hrs at 250° C. |
|---|---|---|---|---|---|---|---|---|---|---|---|
| 10 Compound A | (n = 0) 99% | 43200 | 14600 | 2.9 | 0.12 | 0.016 | 0.089 | 0.13 | 84 | 31–31.5 | ≠0.05 |
| 11 Compound C | (n = 1) 99% | 50800 | 14200 | 3.5 | 0.12 | 0.067 | 0.09 | 0.10 | 83.8 | 31–31.5 | ≠0.1 |
| 12 Compound E | (n = 2) 99% | 38100 | 10300 | 3.7 | 0.12 | 0.076 | 0.09 | 0.13 | 81.6 | 31 | ≠0.15 |

EXAMPLE 13

Bisphenol A (99% moles) and methyl and sodium bis (hydroxy-4-phenyl) 1.1 ethyl phosphonate (1% mole) copolycarbonate, produced by the same procedure as in Example 6, with the use of a chain-limiting agent.

Using the same apparatus as in Example 1, but with a 2-liter balloon-flask, 33.58 g bisphenol A (0.1472 mole) and 0.5 g methyl and sodium bis (hydroxy-4-phenyl) 1.1 ethylphosphonate ($1.52 \times 10^{-3}$ moles) were dissolved in 600 ml of an 0.75 N soda solution.

3 g of 98% triphenylbenzylphosphonium chloride ($7.7 \times 10^{-3}$ moles), and 0.21 g phenol ($2.25 \times 10^{-3}$ moles, i.e. 1.6 molar ratio to total bisphenols), and 300 ml methylene chloride, were then added in turn to the solution.

The reaction mixture was cooled in a flow of nitrogen to approximately 5° C., then 90 ml of a toluene solution containing 20% weight of phosgene (0.17 mole) were added while the mixture was agitated strongly. The same procedure as in Example 6 was then adopted.

After 1 hour's polycondensation at 30° C., the mixture was diluted with 400 ml CH$_2$Cl$_2$, and decanted. The organic phase was then washed until the water used for washing became neutral, and poured into 2 liters of ether.

The polycarbonate precipitate was drained, and dried at 100° C., at reduced pressure, for 24 hours.

There was a 76% yield of polycarbonate.

Molecular weights (by GPC):

Mw = 27 000
Mn = 11 400
I = 2.4

| Elementary analysis: | Calculated % | Experimental % |
|---|---|---|
| Phosphorus | 0.12 | 0.0307 |
| Sodium | 0.089 | 0.14 |

LOI = 32

EXAMPLES 14 and 15

Copolycarbonates of bisphenol A and methyl and potassium bis (hydroxy-4-phenyl) alkylphosphonate with the following structure:

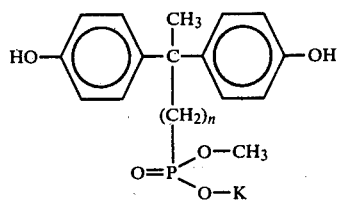

where
n=0 (compound B)
n=1 (compound D).

Copolycarbonate compositions contained 99% moles bisphenol A to 1% moles methyl and potassium bisphenol phosphonate. Tests were performed on 0.1 mole of dihydroxylated compounds. The procedure was the same as in Example 1, except that 150 ml of a 1.6 N solution of K O H was used instead of a soda solution.

Results are shown in Table 4: Copolycarbonates of bisphenol A and methyl and potassium bisphenol phosphonates with the following structure:

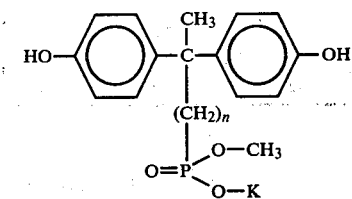

where
n=0 (compound B)
n=1 (compound D)

EXAMPLES 16 to 19

Copolycarbonates of bisphenol A and methyl and potassium bisphenol phosphonates with the following structure:

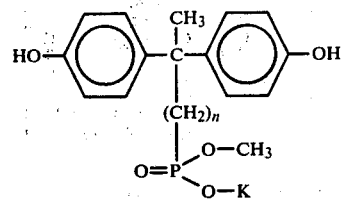

Copolycarbonate compositions contained 0.5 to 2% moles bisphenol phosphonates. Tests were performed on 0.1 mole dihydroxylated compounds, using the same procedure as in Example 1. Results are shown in Table 5: Copolycarbonates of bisphenol A and methyl and potassium bisphenol phosphonates with the following structure:

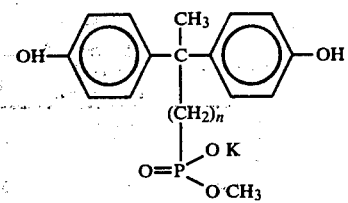

where
n=0 (compound B)
n=1 (compound D).

TABLE IV

| Example No. | Molar % Bisphenol A / Bisphenol phosphonate | GPC Mw | Mn | I | Phosphorus Calc. % | Exper. % | Potassium Calc. % | Exp. % | Yield % | Δ P % 2 hrs at 250° C. | LOI |
|---|---|---|---|---|---|---|---|---|---|---|---|
| 14 Compound B | (n = 0) 99% | 50300 | 4300 | 3.5 | 0.122 | 0.002 | 0.153 | 0.01 | 85 | ≠0 | 32.5 |
| 15 Compound D | (n = 1) 99% | 33700 | 12300 | 2.7 | 0.12 | 0.004 | 0.15 | 0.02 | 84.9 | 1.35 | 32 |

TABLE V

| Example No. | Molar % Bisphenol A / Bisphenol phosphonate | GPC Mw | Mn | I | Phosphorus Calc. % | Exper. % | Potassium Calc. % | Exper. % | Sodium % | Yield % | Δ P % 2 hrs at 250° C. | LOI |
|---|---|---|---|---|---|---|---|---|---|---|---|---|
| 16 Compound B | (n = 0) 99% | 42300 | 14300 | 2.9 | 0.12 | 0.082 | 0.15 | 0.11 | 0.10 | 81.5 | 0.25 | 34–35 |
| 17 Compound D | (n = 1) 99.5% 0.5% | 59100 | 18800 | 3.1 | 0.063 | 0.072 | 0.076 | 0.07 | 0.11 | 86 | | 34–35 |
| 18 Compound D | (n = 1) 99% | 35000 | 12700 | 2.7 | 0.12 | 0.0035 | 0.15 | 0.12 | 0.065 | 86.8 | 0.85 | 33–34 |
| 19 Compound D | (n = 1) 98% 2% | 27000 | 10700 | 2.5 | 0.24 | 0.0037 | 0.301 | 0.055 | 0.105 | 85.8 | 0.45 | 34 |

EXAMPLE 20

Copolycarbonate of bisphenol A (99% moles) and ethyl and potassium bis (hydroxy-4-phenyl) 2.2 propylphosphonate (1% moles).

Conditions were the same as for Example 2.
There was an 83.5% yield of copolycarbonate.

| Elementary analysis: | Calculated % | Experimental % |
|---|---|---|
| Phosphorus | 0.12 | |
| Potassium | 0.151 | 0.13 |
| Sodium | 0 | 0.08 |

LOI = 35

EXAMPLE 21

Copolycarbonate containing 95 mole % bisphenol A 4 mole % dimethyl bis(hydroxy-4-phenyl)2.2propylphosphonate and 1 mole % methyl and potassium bis(-hydroxy-4-phenyl)-2.2propylphosphonate.

Test performed on 0.1 mole of hydroxylated compounds.

The procedure was similar to that used in Example 1.
There was an 84% yield of copolycarbonate.

Molecular weights (GPC):

$\overline{M}_w = 33\,100$ $\overline{M}_n = 12\,300$ $I = 2.7$

| Elementary analysis: | Calculated % | Experimental % |
|---|---|---|
| Phosphorus | 0.59 | 0.32 |
| Potassium | 0.14 | 0.02 |

LOI = 30

The (co)popycarbonates according to the invention have a weight average molecular weight from 10 000 to 100 000, and preferably from 15 000 to 60 000, a glass transition point from 130° C. to 160° C., and a phosphorus content between 0.01% and 9% by weight of the (co)polycabonate.

The weight average molecular weight ($\overline{M}_w$) as well as the number average molecular weight ($\overline{M}_n$) are determined by a gel permeation chromatography method (GPC method) as indicated in more details hereinbefore. These (co)polycarbonates are useful in many fields, such as electrical industries, household appliances, aeronautical engineering. For instance they can be used for making plate connectors, switches, covers for fuse holders, plugs, part of control panels on television receivers. They are also suitable to form the housing of electric motors or of various electric household appliances such as mixers, vacuum cleaners.

Summarizing the (co)polycarbonates according to the invention are fire-resistant polycarbonates or copolycarbonates containing (a) 0.5 to 100 mole % of units (A) having the general formula

where E represents the divalent group deriving, by loss of the hydrogen atoms of the hydroxy groups, from a diester of a bis(hydroxy-4-phenyl)alkylphosphonic acid with the formula (I):

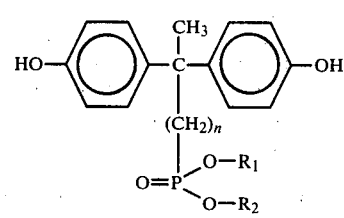

where n=1,2 or 3, $R_1$ and $R_2$ are selected from the group consisting of a methyl radical and an ethyl radical, (b) 0 to 5 mole % of units (B) having the general formula

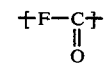

where F represents the divalent group deriving, by loss of the hydrogen atoms of the hydroxy groups, from an alkaline hemiester of a bis(hydroxy-4-phenyl)alkylphosphonic acid with the formula (II)

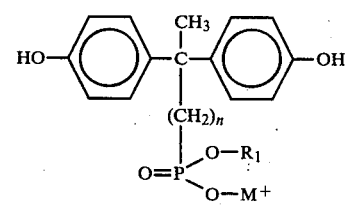

where n=0,1,2 or 3, $R_1$ is a methyl or ethyl radical and M is an alkali metal such as sodium or potassium, and (c) 99.5 to 0 mole % of units (C) having the formula

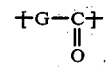

where G is the divalent radical deriving from a bisphenol other than those with formula (I) and (II), for instance bis(hydroxy-4-phenyl)2.2 propane also called bisphenol A, by loss of the hydrogen atoms of the hydroxy groups; said (co)polycarbonates further having a weight average molecular weight ($M_w$), a glass transition point, and a phosphorus content within the ranges defined above.

In particular these (co)polycarbonates include:
polycarbonates only consisting of units (A);
copolycarbonates consisting of units (A) together with units (B), the amount of unit (B) in the copolycarbonate being up to 5 mole % and preferably ranging from 0.5 to 2 mole %;
copolycarbonates consisting of 0.5 to 99.5 mole % and preferably 10 to 75 mole % of units (A) and 99.5 to 0.5 mole % and preferably 90 to 25 mole % of units (C), and for instance of units (C) for which the divalent group G derives from bisphenol A;
copolycarbonates consisting of 0.5 to 2 mole % of units (B) and 99.5 to 98 mole % of units (C), and for instance of units (C) for which the divalent group G derives from bisphenol A; and
copolycarbonates consisting of 0.5 to 99.5 mole % of units (A) and 99.5 to 0.5 mole % of units (C) together with units (B), the amount of units (B) being up to 5 mole % and preferably between 0.5 to 2 mole % of the copolycarbonate.

Naturally, this invention is in no way confined to the Examples and embodiments described above, many variant forms are possible for someone skilled in the art, depending on application and without any departure from the spirit of the invention.

What is claimed is:

1. New fire-resistant (co)polycarbonates, the macromolecular chain of which comprises recurrent functions derived from alkaline diesters or hemiesters of bis (hydroxy-4-phenyl) alkylphosphonic acids, with the following general formula (A) or (B):

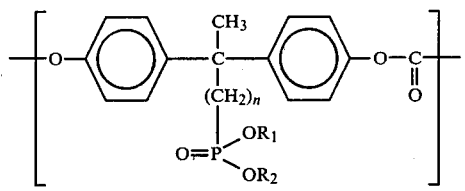

(A) where
n=1, 2 or 3; and
$R_1$ and $R_2$ is a methyl or ethyl radical;

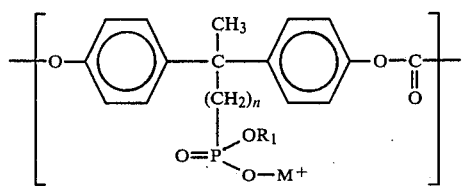

(B) where
n=0, 1, 2 or 3;
$R_1$ is a methyl or ethyl radical; and
M is a sodium or potassium alkaline metal;
these (co)polycarbonates being characterized by the fact that they are produced by interfacial reaction in a phosgene solution:
with a bis (hydroxy-4-phenyl) alkylphosphonic acid diester, used on its own or mixed with another bisphenol in a molar proportion of 10 to 75% total condensation monomers;
or with an alkaline hemiester of sodium or potassium, used on its own or mixed with another bisphenol, in the proportion of 0.5 to 2% total condensation monomers.

2. Polycarbonates as defined in claim 1, in which the bisphenol phosphonate is diethyl bis (hydroxy-4-phenyl) 2.2 propylphosphonate.

3. Polycarbonates as defined in claim 1, in which the bisphenol phosphonate is dimethyl bis (hydroxy-4-phenyl) 2.2 propylphosphonate.

4. Polycarbonates as defined in claim 1, in which the bisphenol phosphonate is dimethyl bis (hydroxy-4-phenyl) 3.3 butylphosphonate.

5. Copolycarbonates as defined in claim 1, in which the bisphenol used for copolycondensation with bis (hydroxy-4-phenyl) acid alkaline hemiesters or diesters is bisphenol A or bis (hydroxy-4-phenyl) 2.2 propane.

6. Copolycarbonates as defined in either claim 1 or 5, in which the bisphenol phosphonate used for copolycondensation with bisphenol A is diemthyl bis (hydroxy-4-phenyl) 2.2 propylphosphonate.

7. Copolycarbonates as defined in either claim 1 or 5, in which the bisphenol phosphonate used for copolycondensation with bisphenol A is methyl and sodium bis (hydroxy-4-phenyl) 1.1 ethylphosphonate.

8. Copolycarbonates as defined in either claim 1 or 5, in which the bisphenol phosphonate used for copolycondensation with bisphenol A is methyl and sodium bis (hydroxy-4-phenyl) 2.2 propylphosphonate.

9. Copolycarbonates as defined in either claim 1 or 5, in which the bisphenol phosphonate used for copolycondensation with bisphenol A is methyl and sodium bis (hydroxy-4-phenyl) 3.3 butylphosphonate.

10. Copolycarbonates as defined in either claim 1 or 5, in which the bisphenol phosphonate used for copolycondensation with bisphenol A is methyl and potassium bis (hydroxy-4-phenyl) 1.1 ethylphosphonate.

11. Copolycarbonates as defined in either claim 1 or 5, in which the bisphenol phosphonate used for copolycondensation with bisphenol A is methyl and potassium bis(hydroxy-4-phenyl)2.2 propylphosphonate.

12. Copolycarbonates as defined in either claim 1 or 5, in which the bisphenol phosphonate used for copolycondensation with bisphenol A is ethyl and potassium bis(hydroxy-4-phenyl)2.2 propylphosphonate.

13. New fire-resistant (co)polycarbonates containing (a) 0.5 to 100 mole % of units (A) having the general formula

where E represents the divalent group deriving, by loss of the hydrogen atoms of the hydroxy groups, from a diester of a bis(hydroxy-4-phenyl) alkylphosphonic acid with the formula (I):

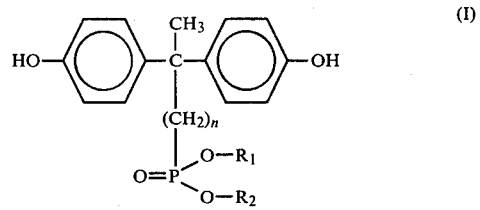

where n=1, 2 or 3 and $R_1$ and $R_2$ are selected from the group consisting of a methyl radical and an ethyl radical; (b) 0 to 5 mole % of units (B) having the general formula

where F represents the divalent group deriving, by loss of the hydrogen atoms of the hydroxy groups, from an alkaline hemiester of a bis(hydroxy-4-phenyl) alkylphosphonic acid with the formula (II):

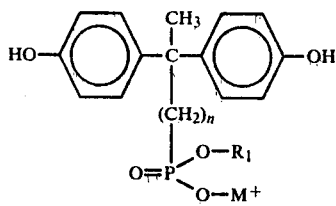
(II)

where n=0, 1, 2 or 3, $R_1$ is a methyl or ethyl radical, and M is an alkali metal such as sodium or potassium; and (c) 99.5 to 0 mole % of units (C) having the formula

where G is the divalent radical deriving from a bisphenol other than those with formula (I) and (II), for instance bisphenol A, by loss of the hydrogen atoms of the hydroxy groups, said (co)polycarbonates having a weight average molecular weight from 10 000 to 100 000, preferably from 15 000 to 60 000, a glass transition point from 130° to 160° C., and a phosphorus content between 0.01% to 9% by weight of the (co)polycarbonate.

14. Polycarbonates according to claim 13, only consisting of units (A).

15. Copolycarbonates according to claim 13, consisting of units (A) together with units (B), the amount of units (B) in the copolycarbonate being up to 5 mole %, and preferably ranging from 0.5 to 2 mole %.

16. Copolycarbonates according to claim 13, consisting of 10 to 75 mole % of units (A) and 90 to 25 mole % of units (C), and preferably of units (C) for which the divalent group G derives from bisphenol A.

17. Copolycarbonates according to claim 13, consisting of 0.5 to 2 mole % of units (B) and 99.5 to 98 mole % of units (C), and preferably of units (C) for which the divalent group G derives from bisphenol A.

18. Copolycarbonates according to claim 13, consisting of 0.5 to 99.5 mole % of units (A) and 99.5 to 0.5 mole % of units (C).

19. Copolycarbonates according to claim 13 consisting of 0.5 to 99.5 mole % of units (A) and 99.5 to 0.5 mole % of units (C) together with units (B), the amount of units (B) being up to 5 mole % and preferably between 0.5 to 2 mole % of the copolycarbonate.

* * * * *